United States Patent [19]
Charleson

[11] Patent Number: 4,880,615
[45] Date of Patent: Nov. 14, 1989

[54] STABILIZED RADIOPHARMACEUTICAL COMPOSITIONS
[75] Inventor: F. Peter Charleson, Kirkland, Canada
[73] Assignee: Merck & Co., Inc., Rahway, N.J.
[21] Appl. No.: 276,253
[22] Filed: Nov. 25, 1988
[51] Int. Cl.$^4$ ............... A61K 49/02; C09K 15/22; C09K 15/06
[52] U.S. Cl. ............... 424/1.1; 252/403; 252/407
[58] Field of Search ............... 414/1.1; 252/403, 407
[56] References Cited

U.S. PATENT DOCUMENTS

| | | | |
|---|---|---|---|
| 4,233,284 | 11/1980 | Fawzi | 424/1.1 |
| 4,243,652 | 1/1981 | Francis | 424/1.1 |
| 4,364,920 | 12/1982 | Winchell | 424/1.1 |
| 4,401,646 | 8/1983 | Rhodes et al. | 424/1.1 |
| 4,489,053 | 12/1984 | Azuma et al. | 424/1.1 |
| 4,793,987 | 12/1988 | Henderson et al. | 424/1.1 |

FOREIGN PATENT DOCUMENTS 96-930A 6/1982 European Pat. Off. .
96-931A 6/1982 European Pat. Off. .
96-934A 6/1982 European Pat. Off. .

OTHER PUBLICATIONS

Chem. Abstracts, vol. 73, 1970, 69846e, Murakami et al.

Primary Examiner—John S. Maples
Attorney, Agent, or Firm—Frank S. Chow; Hesna J. Pfeiffer

[57] ABSTRACT

Radiolytic decomposition of a radiopharmaceutical compositions containing radioactive iodine are stabilized by the incorporation therein of an effective amount of ascorbic acid, nicotinamide, nicotinic acid or combinations thereof.

5 Claims, No Drawings

STABILIZED RADIOPHARMACEUTICAL COMPOSITIONS

BACKGROUND OF THE INVENTION

The present invention relates to stabilized radiopharmaceutical compositions containing radioactive iodine. It also includes within its scope a method for stabilizing the radiolytic decomposition of radiopharmaceutical compositions containing radioactive iodine.

Pharmaceutical compositions containing radioisotopes have many medical applications. These radiopharmaceuticals are useful as therapeutic agents or as diagnostic tools.

There are many commercially available radiopharmaceuticals containing isotopes such as iodine or cobalt useful in these applications. These preparations include for example I-131-ortho-Iodo-Hippuric Acid as a diagnostic tool for the determination of kidney function; Tc-99m Calcium Phytate Injection for renal and liver imaging and gold Au 198 injection for the treatment of neoplastic diseases and so on. Like all radioactive substances, these radiopharmaceuticals will undergo radiolytic decomposition as a result of spontaneous decay. Thus, for example $^{123}$I have a radiological half-life of 13.3 hours $^{198}$Au has a radiological half-life of about 2.7 days, and $^{59}$Fe has a radiological half-life of 45 days and so on. In order to decrease radiolytic decomposition, additives such as antioxidants, antibacterials and stabilizers have been incorporated in these compositions.

Antibacterial agents include for example mixtures of methylparaben and propylparaben; antioxidants include for example sodium bisulfite and sodium metabisulfite. Stabilizers to retard radiolytic decomposition include for example p-aminobenzoic acid, pyridoxine, pyridoal, ethyl gallate, propyl gallate and riboflavin-5-phosphate.

I have found that ascorbic acid, nicotinic acid or nicotinamide or their salts, amides, esters or complexes either alone or in combination when incorporated into radio pharmaceuticals containing radioactive iodine in a manner described below unexpectedly retard the radiolytic decomposition caused by radioactive decay of Iodine thereby prolonging their useful shelf-life.

BRIEF DESCRIPTION OF THE PRIOR ART

Chemical Abstract 73: 698 46e (1970) mentions B$_{12}$ injection photostabilized by the addition of protoporphyrine Na salt, hematoporphyrin, Cu chlorophyllin, nicotinamide, or p-aminobenzoic acid.

European Patent 96-931A, 96-930A and 96-934A disclosed the use of nicotinamide or nicotinic acid as stabilizer for technetium.

SUMMARY OF THE INVENTION

According to the present invention, there is provided stabilized radiopharmaceuticals containing beta or gamma-emitting compounds with radioactive iodine atoms and an effective amount of ascorbic acid, nicotinamide, nicotinic acid or their salts, amides, esters, or complexes either alone or a combination of ascorbic acid with nicotinic acid or nicotinamide as stabilizers against radiolytic decomposition.

DETAILED DESCRIPTION OF THE INVENTION

Broadly speaking, the stabilized radiopharmaceutical compositions of the present invention are prepared by adding an effective amount of ascorbic acid, nicotinic acid, nicotinamide or their salts, amides, esters or complexes either alone or in combination to the selected radiopharmaceutical composition to be stabilized. In a typical formulation, about 16 mg per ml of nicotinic acid or nicotinamide are added to the selected composition by mixing at room temperature until completely dissolved.

When ascorbic acid is the selected stabilizer, 1 to 5% based on the weight of the radiopharmaceutical is used. In the case of a combination with nicotinic acid or nicotinamide ascorbic acid is added in equimolar amounts with nicotinic acid or nicotinamide.

The composition may optionally contain other agents such as antioxidants, antibacterial agents as described above.

Nicotinamide is the preferred stabilizer. The term radio pharmaceuticals used herein and in the Claims means compositions containing radioisotopes of iodine e.g. 123$_I$, 125$_I$, 131$_I$, and 211$_{AT}$ (Astatine-211) and the like. Compositions containing $^{131}$I such as $^{131}$I-MIBG (meta-iodo-benzylquanidine) was stabilized with previously known stabilizers and with nicotinamide. The results obtained are tabulated in Table I.

TABLE I

| Solution No. | Activity (mCi) | Volume (mL) | Specific Concent'n (mCi/mL) | DILUENT COMPOSITION Stabilizer | Concentration (mg/mL) | RADIOCHEMICAL PURITY (%) Storage Time (days) | | | | | | | | | | | | | | |
|---|---|---|---|---|---|---|---|---|---|---|---|---|---|---|---|---|---|---|---|---|
| | | | | | | 0 | 1 | 2 | 4 | 5 | 6 | 7 | 8 | 9 | 11 | 12 | 11 | 14 | 15 | 16 | 18 |
| 33-1 | 29.4 | 14.7 | 2 | PABA | 4 | 98 | 98 | — | 98 | — | — | — | — | — | — | 92 | 90 | 90 | — | — | 90 |
| 33-2 | 57 | 13 | 4.4 | " | 4 | 98.5 | — | — | 93 | 93 | 92 | 91 | — | — | 90 | — | — | — | 89 | — | — |
| 41 | 4 | 1 | 4 | PABA | 4 | 96 | 95 | — | — | 93 | — | — | — | 92 | — | 91 | — | 89 | — | — | — |
| 42 | 4 | 1 | 4 | " | 5 | " | 96 | — | — | 94 | — | — | — | 94 | — | — | — | 91 | 90 | — | — |
| 43 | 4 | 1 | 4 | " | 6 | " | 95 | — | — | 94 | — | — | — | 93 | — | — | — | 92 | — | 92 | — |
| 44 | 4 | 1 | 4 | Pyridoxal | 4 | " | 95 | — | — | 93 | — | — | — | 92 | — | 89 | — | — | — | — | — |
| 45 | 8 | 1 | 8 | PABA | 8 | " | 95 | — | — | 93 | — | — | — | 91 | — | 88 | — | — | — | — | — |
| 46 | 8 | 1 | 8 | " | 7 | " | 95 | — | — | 92 | — | — | — | 91 | — | 87 | — | — | — | — | — |
| 47 | 4 | 0.5 | 8 | Pyridoxal | 8 | 97 | 96 | — | — | 95 | — | — | — | — | — | — | 90 | — | — | — | — |
| 48 | 4 | 1 | 4 | " | 4 | " | 97 | — | — | — | — | — | 95 | — | — | — | 94 | — | — | — | 93 |
| 49 | 4 | 0.5 | 8 | Pyridoxine | 8 | " | 96 | — | — | 94 | — | — | 92 | — | 91 | — | 90 | — | 89 | — | — |
| 50 | 4 | 1 | 4 | " | 4 | " | 97 | — | — | 95 | — | — | — | — | — | — | 94 | — | — | — | 93 |
| 51 | 4 | 0.5 | 8 | FMN*$^3$ | 8 | " | 96 | — | — | 89 | — | — | — | — | — | — | — | — | — | — | — |
| 52 | 4 | 1 | 4 | " | 4 | " | 96 | — | — | 93 | 93 | — | — | — | 91 | — | — | — | — | — | 90 |
| 53 | 4 | 0.5 | 8 | Eth—Gal*$^4$ | 8 | " | 96 | — | — | 94 | — | — | 92 | — | — | — | 88 | — | — | — | — |
| 54 | 4 | 1 | 4 | " | 4 | " | 97 | — | — | — | — | — | 93 | — | — | — | 91 | — | 93 | — | 91 |
| 55 | 4 | 0.5 | 8 | Niacinamide | 8 | " | 96 | — | — | 93 | 93 | — | 91 | — | 90 | — | — | — | — | — | — |
| 33-5 | 54.4 | 6.8 | 8 | Pyridoxine | 8 | 85 | 98 | 97 | — | 95 | — | — | — | 93 | — | 92 | — | — | — | — | — |

TABLE I-continued

| Solution No. | Activity (mCi) | Volume (mL) | Specific Concent'n (mCi/mL) | DILUENT COMPOSITION Stabilizer | Concentration (mg/mL) | RADIOCHEMICAL PURITY (%) Storage Time (days) | | | | | | | | | | | | | | | | |
|---|---|---|---|---|---|---|---|---|---|---|---|---|---|---|---|---|---|---|---|---|---|---|
| | | | | | | 0 | 1 | 2 | 4 | 5 | 6 | 7 | 8 | 9 | 11 | 12 | 11 | 14 | 15 | 16 | 18 |
| 33-6 | 54.8 | 6.8 | 8 | Niacinamide | 16 | 98 | 98 | — | 96 | — | — | — | 95 | — | 94 | — | — | — | — | — | — | |

*All have 0.005M acetate buffer pH 5.0
*²Stored in the dark at room temperature.
*³Flavin monomucleotide.
*⁴Ethyl gallate Referring to the above table, it can be readily appreciated that the solution stabilized by nicotinamide according to the present invention showed enhanced shelf-life as measured by percent of radiochemical purity over known stabilizers e.g. p-aminobenzoic acid (PABA) pyridoxal, etc.

I have also found that the use of nicotinamide or nicotinic acid has additional advantages. Thus, when used in combination with radiopharmaceuticals for therapeutic use, they do not add to the cost of manufacture as they are readily available and they are relatively less toxic than other known stabilizers.

Although the exact mechanism of the stabilizing effect of ascorbic acid, nicotinic acid or nicotinamide is not established, it is believed that these compounds will act as scavengers for radicals produced by radiolytic decomposition. Thus, the incorporation of one of these compounds alone or in combination in a radiopharmaceutical reduces the damage due to radiolysis.

What is claimed is:

1. A stablized radiopharmaceutial composition comprising a molecule containing a radioactive iodine atom and a stabilizer selected from the group consisting of ascorbic acid, nicotinamide and its corresponding amides, or a mixture of ascorbic acid and nicotinamide and its amides, in a sufficient amount to stabilize against radiolytic decomposition.

2. A composition according to claim 1 in which the radioactive iodine is $^{131}$ iodine.

3. A composition according to claim 1 which contains equimolar amounts of ascorbic acid and nicotinamide.

4. A composition according to claim 1 wherein the stabilizer is nicotinamide.

5. A composition according to claim 4 in which nicotinamide is present at a concentration of about 16 mg/ml of said composition.

* * * * *

UNITED STATES PATENT AND TRADEMARK OFFICE
CERTIFICATE OF CORRECTION

PATENT NO.　：　4,880,615

DATED　　　：　November 14, 1989

INVENTOR(S)：　F. PETER CHARLESON, Kirkland, Canada

It is certified that error appears in the above-identified patent and that said Letters Patent is hereby corrected as shown below:

On the title page, item [73]:

AS ASSIGNEE

Please delete "Merck & Co., Inc., Rahway, N.J."

and replace it with "MERCK FROSST CANADA, Inc.,

Kirkland, Quebec, Canada".

Signed and Sealed this

Thirteenth Day of November, 1990

Attest:

HARRY F. MANBECK, JR.

Attesting Officer　　　　Commissioner of Patents and Trademarks